(12) United States Patent
Kurosaki et al.

(10) Patent No.: US 11,097,460 B2
(45) Date of Patent: Aug. 24, 2021

(54) BALLOON WRAPPING APPARATUS

(71) Applicant: TERUMO KABUSHIKI KAISHA, Tokyo (JP)

(72) Inventors: Yasuo Kurosaki, Kanagawa (JP); Hiroshi Goto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 107 days.

(21) Appl. No.: 15/928,285

(22) Filed: Mar. 22, 2018

(65) Prior Publication Data

US 2018/0207854 A1    Jul. 26, 2018

Related U.S. Application Data

(63) Continuation of application No. PCT/JP2016/078037, filed on Sep. 23, 2016.

(30) Foreign Application Priority Data

Sep. 25, 2015  (JP) .............................. JP2015-188033

(51) Int. Cl.
*B29C 53/08*    (2006.01)
*B29C 53/82*    (2006.01)
(Continued)

(52) U.S. Cl.
CPC .......... *B29C 53/08* (2013.01); *A61M 25/1034* (2013.01); *A61M 25/1038* (2013.01);
(Continued)

(58) Field of Classification Search
CPC ..... B29C 53/08; B29C 70/682; B29C 53/821; B29C 53/566; B29C 51/10; B29C 33/76;
(Continued)

(56) References Cited

U.S. PATENT DOCUMENTS 5,350,361 A    9/1994   Tsukashima et al.
6,296,655 B1   10/2001  Gaudoin et al.
(Continued)

FOREIGN PATENT DOCUMENTS

JP    2002-512862 A    5/2002
JP    2004-525704 A    8/2004
(Continued)

OTHER PUBLICATIONS

Machine Solutions Inc., YouTube Video, "MSI FFS875s Long PTA Balloon Catheter Pleating & Folding, Wrapping & Fluting", https://www.youtube.com/watch?v=9smmnWeolUA, Jun. 29, 2010, screenshots at 00:20 and 00:54 attached. (Year: 2010).*
(Continued)

*Primary Examiner* — Michael N Orlando
*Assistant Examiner* — Christopher W Raimund
(74) *Attorney, Agent, or Firm* — Buchanan Ingersoll & Rooney PC

(57) ABSTRACT

A balloon wrapping apparatus is disclosed by which a balloon can be accurately positioned and inserted in relation to a pleating section. The balloon wrapping apparatus for wrapping a balloon provided at a distal portion of an elongated shaft includes: a pleating section that forms the balloon with wing shapes; a folding section that folds the wing shapes formed in the balloon along a circumferential direction; a support base that supports a portion other than the distal portion of the shaft, and that makes the distal portion of the shaft insertable into the pleating section and the folding section; and a core metal member to be inserted in the shaft. The core metal member is inserted in the shaft from a distal end position of the balloon to at least the proximal side of a proximal end position of the balloon.

18 Claims, 12 Drawing Sheets

(51) Int. Cl.
*B29C 53/20* (2006.01)
*A61M 25/10* (2013.01)
*B29C 33/76* (2006.01)
*B29C 51/10* (2006.01)
*B29C 53/56* (2006.01)
*B29C 70/68* (2006.01)
*B29C 53/84* (2006.01)
*B29L 31/00* (2006.01)

(52) U.S. Cl.
CPC .............. *B29C 33/76* (2013.01); *B29C 51/10* (2013.01); *B29C 53/086* (2013.01); *B29C 53/20* (2013.01); *B29C 53/566* (2013.01); *B29C 53/82* (2013.01); *B29C 53/821* (2013.01); *B29C 70/682* (2013.01); *A61M 2025/105* (2013.01); *B29C 53/84* (2013.01); *B29L 2031/7543* (2013.01)

(58) Field of Classification Search
CPC ....... B29C 53/20; B29C 53/086; B29C 53/82; B29C 53/84; A61M 25/1038; A61M 25/1034; A61M 2025/105; B29L 2031/7543
See application file for complete search history.

(56) References Cited

U.S. PATENT DOCUMENTS

| | | | |
|---|---|---|---|
| 7,762,804 B1 | 7/2010 | Stupecky | |
| 2002/0163104 A1* | 11/2002 | Motsenbocker | .. A61M 25/1002 264/320 |
| 2011/0118660 A1* | 5/2011 | Torrance | ........ A61B 17/320758 604/35 |
| 2012/0100279 A1 | 4/2012 | Neumann et al. | |
| 2013/0197563 A1* | 8/2013 | Saab | ..................... A61M 29/02 606/191 |
| 2014/0319750 A1 | 10/2014 | Yanes et al. | |
| 2016/0296969 A1 | 10/2016 | Kurosaki et al. | |

FOREIGN PATENT DOCUMENTS

| | | |
|---|---|---|
| JP | 2006-271678 A | 10/2006 |
| JP | 2013-056071 A | 3/2013 |
| JP | 2014-018493 A | 2/2014 |
| WO | 2015/093585 A1 | 6/2015 |

OTHER PUBLICATIONS

International Search Report (PCT/ISA/210) dated Dec. 20, 2016, by the Japanese Patent Office as the International Searching Authority for International Application No. PCT/JP2016/078037.

Written Opinion (PCT/ISA/237) dated Dec. 20, 2016, by the Japanese Patent Office as the International Searching Authority for International Application No. PCT/JP2016/078037.

English translation of International Search Report issued in International Patent Application No. PCT/JP2016/078037, 2 pages. (dated Dec. 20, 2016).

English translation of Written Opinion issued in International Patent Application No. PCT/JP2016/078037, 6 pages. (dated Dec. 20, 2016).

The extended European Search Report dated Mar. 20, 2019, by the European Patent Office in corresponding European Patent Application No. 16848667.8-1132. (8 pages).

Notice of Reasons for Refusal issued by the Japanese Patent Office in corresponding Japanese Patent Application No. 2017-540920 dated Mar. 9, 2020 (8 pages including partial English translation).

* cited by examiner

FIG. 3
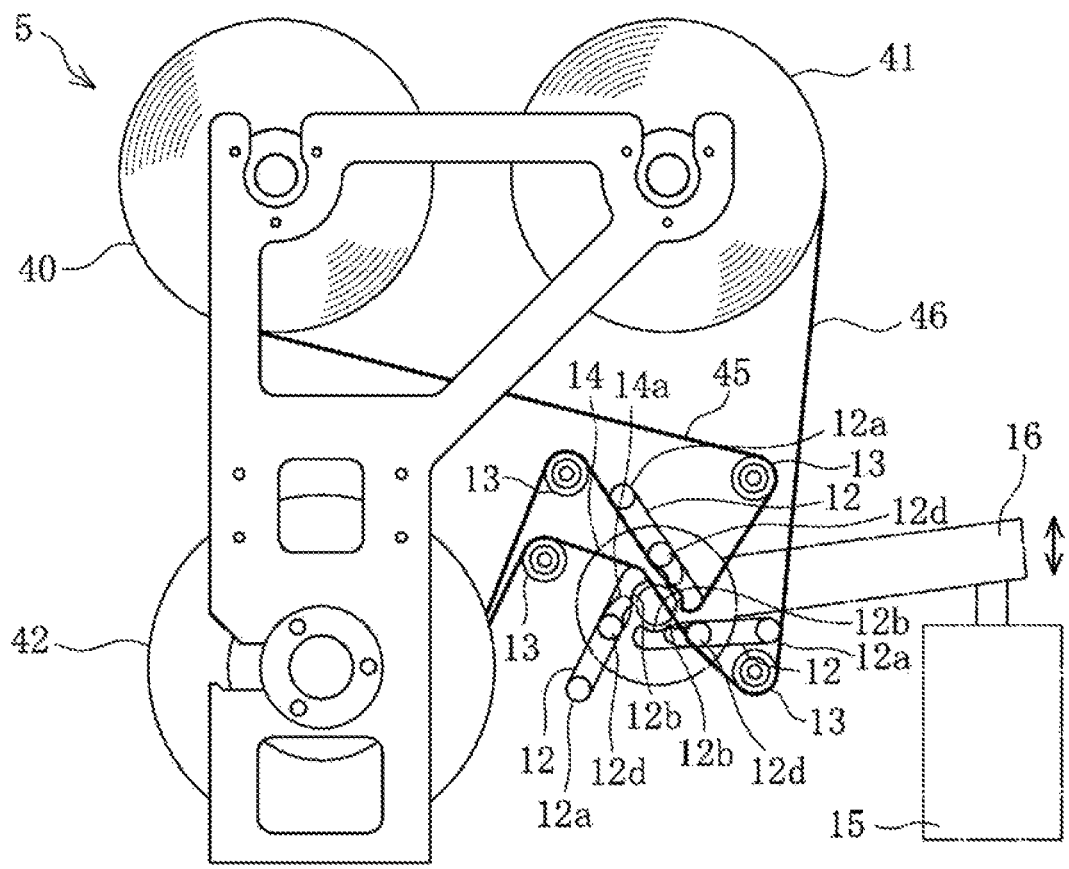
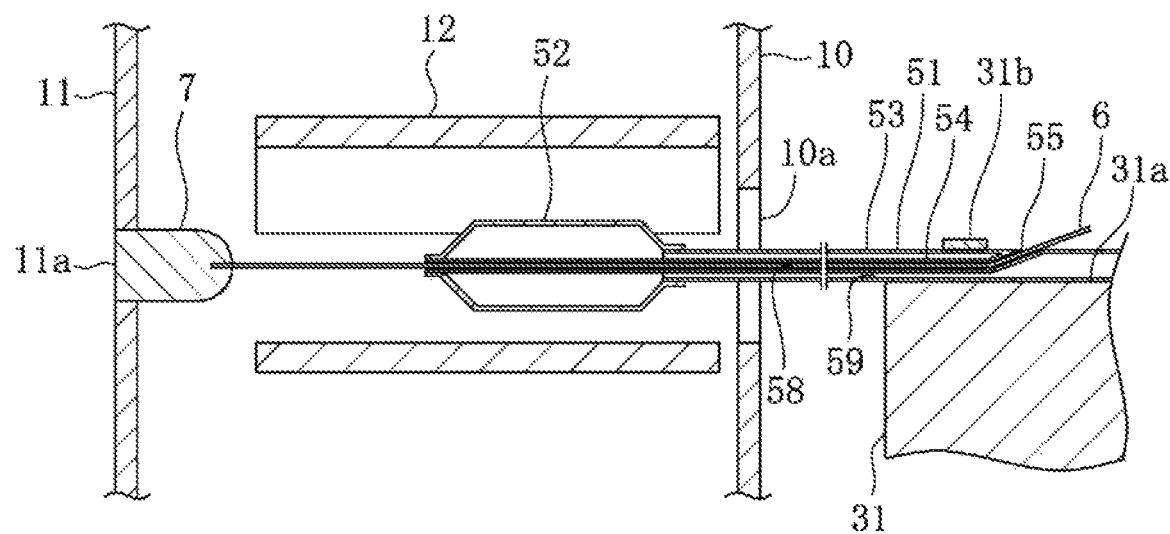
FIG. 4

Table 1

| Conditions | Example 1 | Example 2 | Example 3 | Example 4 | Example 5 |
|---|---|---|---|---|---|
| Diameter/length of balloon | 2.0 mm/40 mm | 4.0 mm/200 mm | 3.0 mm/200 mm | 2.0 mm/200 mm | 6.0 mm/200 mm |
| Material of balloon | Nylon | Nylon | Nylon | Nylon | Nylon |
| Surface condition of balloon catheter | Smooth, non-porous | Smooth, non-porous | Smooth, non-porous | Smooth, non-porous | Smooth, non-porous |
| Amount of paclitaxel | 3.2 µg/mm$^2$ | 3.6 µg/mm$^2$ | 3.6 µg/mm$^2$ | 3.2 µg/mm$^2$ | 3.2 µg/mm$^2$ |
| Diameter/length of core metal member | 0.39 mm/700 mm | 0.38 mm/500 mm | 0.38 mm/500 mm | 0.38 mm/700 mm | 0.48 mm/700 mm |
| Shape of core metal member | Wire-like | Wire-like | Wire-like | Wire-like | Wire-like |
| Material of core metal member | SUS | SUS | SUS | SUS | SUS |
| Material of holding portion | Silicone rubber | Silicone rubber | Silicone rubber | Silicone rubber | Silicone rubber |
| Shape/function of distal support of pleating section | Insertion into distal support | Insertion into distal support | Insertion into distal support | Insertion into distal support | Insertion into distal support |
| Number of blades in pleating section | Three | Three | Three | Three | Four |
| Characteristics of films | Difficult to electrostatically charge, smooth | Difficult to electrostatically charge, smooth | Difficult to electrostatically charge, smooth | Difficult to electrostatically charge, smooth | Difficult to electrostatically charge, smooth |
| Film (material/thickness) | Teflon/0.001 mm | Teflon/0.001 mm | Teflon/0.001 mm | Teflon/0.001 mm | Teflon/0.001 mm |
| Control of pulling by collet chuck | - | - | - | - | - |
| Shape/function of distal support of folding section | Insertion into central portion of distal support | Insertion into central portion of distal support | Insertion into central portion of distal support | Insertion into central portion of distal support | Insertion into central portion of distal support |
| Number of blades in folding section | Ten | Ten | Ten | Ten | Ten |
| Control of pulling by collet chuck | - | - | - | - | - |
| Timing of start of rotation | Point of time when films contacted wings | - | - | Point of time when films contacted wings | - |
| Rotation direction of balloon catheter as viewed from proximal side | Counterclockwise | - | - | Counterclockwise | - |

FIG. 15

Table 2

| Conditions | Example 6 | Example 7 | Example 8 | Example 9 |
|---|---|---|---|---|
| Diameter/length of balloon | 6.0 mm/200 mm | 4.0 mm/200 mm | 4.0 mm/200 mm | 4.0 mm/200 mm |
| Material of balloon | Nylon | Nylon | Nylon | Nylon |
| Surface condition of balloon catheter | Smooth, non-porous | Smooth, non-porous | Smooth, non-porous | Smooth, non-porous |
| Amount of paclitaxel | 3.2 µg/mm$^2$ | 3.2 µg/mm$^2$ | 3.2 µg/mm$^2$ | 3.2 µg/mm$^2$ |
| Diameter/length of core metal member | 0.48 mm/700 mm | 0.48 mm/700 mm | 0.48 mm/700 mm | 0.48 mm/700 mm |
| Shape of core metal member | Wire-like | Hollow | Hollow | Hollow |
| Material of core metal member | SUS | SUS | SUS | SUS |
| Material of holding portion | Silicone rubber | Silicone rubber | Silicone rubber | Silicone rubber |
| Shape/function of distal support of pleating section | Clamping in collet chuck | Clamping in collet chuck | Clamping in collet chuck | Clamping in collet chuck |
| Number of blades in pleating section | Four | Four | Four | Four |
| Characteristics of films | Difficult to electrostatically charge, smooth | Difficult to electrostatically charge, smooth | Difficult to electrostatically charge, smooth | Difficult to electrostatically charge, smooth |
| Film (material/thickness) | Teflon/0.001 mm | Teflon/0.001 mm | Teflon/0.001 mm | Teflon/0.001 mm |
| Control of pulling by collet chuck | Distal support is fixed at prescribed position and then support base is pulled backward by 5 mm | Distal support is pulled further forward by 5 mm from prescribed position and fixed | Distal support is fixed at prescribed position and then support base is pulled backward with force of 5 N | Distal support is pulled further from prescribed position with force of 1 N and fixed |
| Shape/function of distal support of folding section | Clamping in collet chuck | Clamping in collet chuck | Clamping in collet chuck | Clamping in collet chuck |
| Number of blades in folding section | Eight | Twelve | Twelve | Twelve |
| Control of pulling by collet chuck | Distal support is fixed at prescribed position and then support base is pulled backward by 5 mm | Distal support is pulled further forward by 5 mm from prescribed position and fixed | Distal support is fixed at prescribed position and then support base is pulled backward with force of 5 N | Distal support is pulled further from prescribed position with force of 1 N and fixed |
| Timing of start of rotation | Point of time when films contacted wings | Point of time when films contacted wings | Point of time when films contacted wings | Point of time when films contacted wings |
| Rotation direction of balloon catheter as viewed from proximal side | Counterclockwise | Counterclockwise | Counterclockwise | Counterclockwise |

FIG. 16

Table 3

| Conditions | Example 10 | Example 11 | Example 12 | Example 13 |
|---|---|---|---|---|
| Diameter/length of balloon | 3.0 mm/20 mm | 4.0 mm/200 mm | 3.0 mm/200 mm | 2.0 mm/200 mm |
| Material of balloon | Nylon elastomer | Nylon | Nylon | Nylon |
| Surface condition of balloon catheter | Smooth, non-porous | Smooth, non-porous | Smooth, non-porous | Smooth, non-porous |
| Amount of paclitaxel | 3.2 µg/mm$^2$ | 3.6 µg/mm$^2$ | 3.6 µg/mm$^2$ | 3.2 µg/mm$^2$ |
| Diameter/length of core metal member | 0.38 mm/500 mm | 0.38 mm/500 mm | 0.38 mm/500 mm | 0.38 mm/700 mm |
| Shape of core metal member | Wire-like | Wire-like | Wire-like | Wire-like |
| Material of core metal member | SUS | SUS | SUS | SUS |
| Material of holding portion | Silicone rubber | Silicone rubber | Silicone rubber | Silicone rubber |
| Shape/function of distal support of pleating section | Insertion into distal support | Insertion into distal support | Insertion into distal support | Clamping in collet chuck |
| Number of blades in pleating section | Three | Three | Three | Four |
| Characteristics of films | Difficult to electrostatically charge, smooth | - | - | Difficult to electrostatically charge, smooth |
| Film (material/thickness) | Teflon/0.001 mm | None | None | Teflon/0.001 mm |
| Control of pulling by collet chuck | - | - | - | - |
| Shape/function of distal support of folding section | Insertion into distal support | Insertion into distal support | Insertion into distal support | Insertion into distal support |
| Number of blades in folding section | Twelve | Ten | Ten | Ten |
| Control of pulling by collet chuck | - | - | - | - |
| Timing of start of rotation | Point of time when films contacted wings | - | - | - |
| Rotation direction of balloon catheter as viewed from proximal side | Counterclockwise | - | - | - |

FIG. 17

Table 4

| Examples | Presence/absence of films | Size (diameter/length) of balloon | Amount of paclitaxel per unit area [μg/mm$^2$] | | Retention rate of paclitaxel (%) |
|---|---|---|---|---|---|
| | | | After coating | After folding | |
| Example 1 | Present | 2.0 mm/40 mm | 3.2 | 2.8 | 88 |
| Example 2 | Present | 4.0 mm/200 mm | 3.6 | 3.5 | 97 |
| Example 3 | Present | 3.0 mm/200 mm | 3.6 | 3.3 | 92 |
| Example 4 | Present | 2.0 mm/200 mm | 3.2 | 3.1 | 96 |
| Example 5 | Present | 6.0 mm/200 mm | 3.2 | 3.1 | 97 |
| Example 11 | Absent | 4.0 mm/200 mm | 3.6 | 2.8 | 78 |
| Example 12 | Absent | 3.0 mm/200 mm | 3.6 | 2.6 | 72 |

FIG. 18

Table 5

| Examples | Rotation of balloon during folding | Number of drug-coated balloons in which back folding was generated [(Number of drug-coated balloons in which back folding was generated)/(Total number of drug-coated balloons subjected to folding)] | Generation rate of back folding [%] |
|---|---|---|---|
| Example 4 | Performed | 1/142 | 0.7 |
| Example 13 | Not performed | 22/46 | 48 |

FIG. 19

BALLOON WRAPPING APPARATUS

CROSS-REFERENCES TO RELATED APPLICATIONS

This application is a continuation of International Application No. PCT/JP2016/078037 filed on Sep. 23, 2016, which claims priority to Japanese Application No. 2015-188033 filed on Sep. 25, 2015, the entire contents of both of which are incorporated herein by reference.

TECHNICAL FIELD

The present disclosure relates to a balloon wrapping apparatus for wrapping a balloon of a balloon catheter.

BACKGROUND ART

Treatment of a lesion of a blood vessel by use of a catheter has been widely practiced because of little surgical invasiveness. For example, in percutaneous coronary angioplasty (Percutaneous Transluminal Coronary Angioplasty), a balloon catheter can be used for improving blood flow by pushing open a lesion part of a coronary artery. In general, a balloon catheter includes an elongated hollow shaft, a balloon provided on the distal side of the shaft, and a hub provided on the proximal side of the shaft. The balloon catheter may be provided with a drug eluting balloon having a surface coated with a drug.

The balloon of a balloon catheter is required to be as small as possible in diameter when deflated, for good passing properties in a blood vessel. The balloon is formed in a small diameter form by being wrapped at the time of manufacturing the catheter. The wrapping of the balloon is conducted by a pleating step of bending the balloon to form a plurality of wing shapes, for example, three or four wing shapes in the circumferential direction, and a folding step of folding the thus formed wing shapes toward one side in the circumferential direction.

As a conventional balloon wrapping apparatus, there may be mentioned, for example, the one described in JP-T-2004-525704. The balloon wrapping apparatus has a pleating section for performing pleating, and a folding section for performing folding. In addition, the balloon wrapping apparatus has a support base which supports the shaft of the balloon catheter and which is slidable such that the balloon can be inserted into each head.

The pleating section has a plurality of blades in the circumferential direction for shaping the balloon to have the wings. Between the plurality of blades, a space part extending along an insertion direction of the balloon is formed. In addition, the blades can be moved rotationally in such a manner as to change the shape of the space part. The balloon is inserted into the space part between the blades, and the balloon is narrowed by the blades moved rotationally, whereby wing shapes are formed.

The folding section has a plurality of rotatable blades such that the wing shapes formed in the balloon can be folded in the manner of being wrapped around along the circumferential direction. The balloon is inserted into a region surrounded by the plurality of blades, and the blades are moved rotationally such as to close the region between the blades, whereby the wing shapes formed in the balloon are folded along the circumferential direction.

When wrapping the balloon, the balloon catheter is placed on the support base, and the support base is slid toward the pleating section, whereby the balloon is advanced into the pleating section, and pleating is conducted. When the balloon is drawn out of the pleating section, the balloon is subsequently advanced into the folding section, and folding is conducted.

SUMMARY OF INVENTION

For improving passing properties of the balloon, the wing shapes should be formed into an accurate shape on the basis of a predetermined interval along the circumferential direction in wrapping of the balloon. For this purpose, the balloon should be positioned accurately at a center position of the pleating section. If the position of the balloon is deviated from the center position of the pleating section, the wing shapes formed in pleating may not become uniform. In addition, if the position of the balloon is deviated from the center position of the folding section, back folding in which the wing shapes are folded in the reverse direction in the circumferential direction may occur.

When the catheter is placed on the support base and the balloon is inserted into the pleating section, a portion near the distal end of the catheter having the balloon is not supported by the support base, and, therefore, the catheter is bent downward due to balloon's own weight. Accordingly, it is difficult to accurately position the balloon at the center position of the pleating section or the folding section.

A balloon wrapping apparatus is disclosed by which a balloon can be accurately positioned and inserted in relation to a pleating section and a folding section.

A balloon wrapping apparatus according to the present disclosure for achieving the aforesaid object is a balloon wrapping apparatus for wrapping a balloon provided at a distal portion of an elongated shaft, the balloon wrapping apparatus including: a pleating section that forms the balloon with wing shapes; a folding section that folds the wing shapes formed in the balloon along a circumferential direction; a support base that supports a portion other than the distal portion of the shaft, and that makes the distal portion of the shaft insertable into the pleating section and the folding section; and a core metal member to be inserted in the shaft. The core metal member is inserted in the shaft from a distal end position of the balloon to at least a proximal side of a proximal end position of the balloon.

In accordance with an exemplary embodiment, in the balloon wrapping apparatus configured as above, the distal portion of the shaft inclusive of the balloon is supported by the core metal member in such a manner as not to bend. Therefore, the balloon can be accurately positioned and inserted in relation to the pleating section and the folding section. For this reason, the wing shapes of the balloon can be formed uniformly in the circumferential direction in the pleating section, and back folding can be restrained from occurring when the wing shapes are folded in the folding section.

Where the shaft has an inner tube and an outer tube disposed concentrically, with the inner tube extending to a proximal-side end portion of the shaft, and the core metal member has a length of at least twice the length of the balloon, bending of the distal portion of the shaft inclusive of the balloon can be effectively restrained, in an over-the-wire type balloon catheter.

Where the shaft has an inner tube and an outer tube disposed concentrically, with the inner tube having an opening portion that opens to the outside of the outer tube at an intermediate position of the shaft, and the core metal member has a proximal-side end portion exposed to the outside through the opening portion of the inner tube, bending of the distal portion of the shaft inclusive of the balloon can be effectively restrained, in a rapid exchange type balloon catheter.

Where the support base has a holding portion that holds the shaft, and the core metal member has a proximal-side end portion extending to the proximal side of a position at which the shaft is held by the holding portion, the core metal member is held by the holding portion of the support base, so that bending of the shaft on the distal side of the holding portion can be restrained more securely.

Where the core metal member has an outside diameter equal to, or smaller, for example, by 0.01 mm to 0.1 mm than, the inside diameter of the inner tube of the shaft, the core metal member can be smoothly inserted into the inner tube, and the shaft can be securely supported and restrained from bending.

Where the core metal member is longer than the length of the blades of the balloon wrapping apparatus by not less than, for example, 10 mm, the core metal member can be placed on a distal support and the support base, and the shaft of the balloon catheter can be securely supported and restrained from bending.

Where the core metal member is formed in a curved shape in a state before insertion into the shaft, it is possible, by disposing the core metal member in such a manner as to be projected toward a direction opposite to a bending direction of the shaft, to make bending of the shaft and curving of the core metal member cancel each other, and thereby to make the shaft more horizontal.

Where the core metal member has a flat surface portion at a part of a circumferential surface thereof, the core metal member can be assuredly disposed in such a manner that a curving direction of the core metal member is directed in a direction opposite to a bending direction of the shaft.

A balloon wrapping apparatus is disclosed for wrapping a balloon, the balloon wrapping apparatus comprising: an elongated shaft, the elongated shaft having an inner tube and an outer tube disposed concentrically, with the inner tube having an opening portion that opens to outside of the outer tube at an intermediate position of the elongated shaft; a pleating section configured to form the balloon with wing shapes; a folding section configured to fold the wing shapes formed in the balloon along a circumferential direction; a support base configured to support a portion other than the distal portion of the elongated shaft, and make the distal portion of the elongated shaft insertable into the pleating section and the folding section; a core metal member to be inserted in the shaft, wherein the core metal member is inserted in the shaft from a distal end position of the balloon to at least a proximal side of a proximal end position of the balloon, the core metal member having a proximal-side end portion exposed to outside through the opening portion of the inner tube; and wherein the support base has a holding portion configured to hold the elongated shaft, and the core metal member has a proximal-side end portion extending to a proximal side of a position at which the shaft is held by the holding portion.

A balloon wrapping method is disclosed for wrapping a balloon of a balloon catheter provided with the balloon at a distal portion of an elongated shaft, the balloon wrapping method comprising: supporting a portion other than the distal portion of the elongated shaft, and that makes the distal portion of the elongated shaft insertable into a pleating section and a folding section; inserting a core metal member in the elongated shaft, wherein the core metal member is inserted in the shaft from a distal end position of the balloon to at least a proximal side of a proximal end position of the balloon; forming the balloon with wing shapes projecting in radial directions with pleating section; and folding the wing shapes n the balloon along a circumferential direction with the folding section.

BRIEF DESCRIPTION OF THE DRAWINGS

FIG. 3 is a front view representing a layout of blades and a film supplying section in a pleating section.

FIG. 4 is a sectional view of the balloon catheter and the pleating section in a state in which the balloon is inserted in the pleating section.

FIGS. 15-17 are Tables 1-3, which illustrate examples of the present disclosure and comparative examples as disclosed herein, which includes drug-coated balloons of Examples 1 to 13 produced under the conditions as set forth in Tables 1-3.

FIG. 18 is Table 4, which compares Examples 1-5, 11, and 12 to one another including amounts of paclitaxel per unit area after coating and after folding, and a retention rate of paclitaxel for each of the Examples.

FIG. 19 is Table 5, which depicts the number of drug-coated balloons in which back folding was generated, the total number of drug-coated balloons subjected to folding, and generation rate of back folding for Examples 4 and 13.

DETAILED DESCRIPTION

Figure 1:
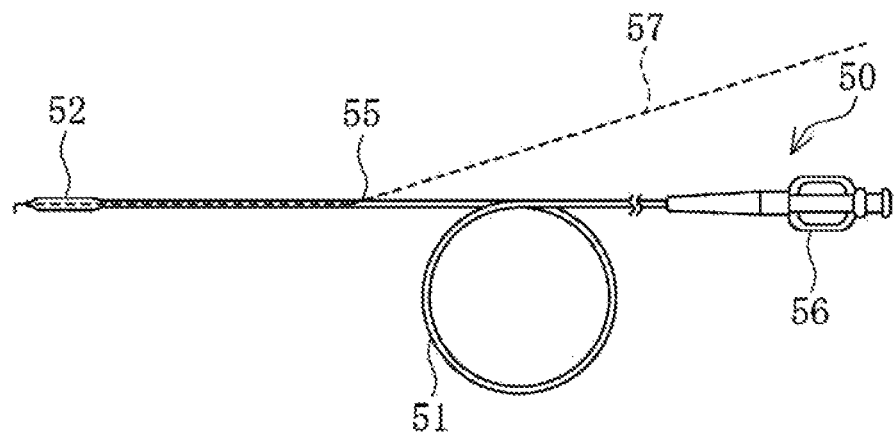
FIG. 1 is a front view of a rapid exchange type balloon catheter.

An exemplary embodiment of the present invention will be described below, referring to the drawings. Note that the dimensional ratios in the drawings may be exaggerated and be different from the actual ratios, for convenience of explanation. Herein, the side of insertion of a balloon catheter 50 into a body lumen will be referred to as "distal end" or "distal side," and the side of an operator's hand operation will be referred to as "proximal end" or "proximal side."

A balloon wrapping apparatus according to the present embodiment is an apparatus capable of wrapping a balloon so as to wrap a balloon 52 around a shaft 51, at the time of manufacturing the balloon catheter 50 having the balloon 52 at a distal portion of the elongated shaft 51.

The balloon catheter to be wrapped may be subjected to hydrophilic coating for the purpose of improving properties for delivery to a lesion part, or may have a balloon surface subjected to a surface treatment such as a plasma treatment or irradiation with UV rays, but this is not particularly restrictive. There can also be used a balloon catheter in which the surface of a balloon has been subjected to a drug coating for delivery of a drug to a lesion part.

In the first place, the balloon catheter 50 will be described. As depicted in FIG. 1, the balloon catheter 50 includes the elongated hollow shaft 51, the balloon 52 provided at a distal-side end portion of the shaft 51, and a hub 56 secured to a proximal-side end portion of the shaft 51.

The length of the balloon 52 in a major axis direction is not particularly limited, and is, for example, greater than approximately 3 mm. Preferably, the length of the balloon in the major axis direction is approximately 20 mm to 400 mm, more preferably 30 mm to 300 mm, and further preferably approximately 40 mm to 200 mm. The diameter of the balloon 52 in a minor axis direction (the direction orthogonal to the major axis direction) is not particularly restricted, and is, for example, preferably not less than 1 mm, more preferably 1 mm to 10 mm, still more preferably 2 mm to 8 mm, and further preferably 2 mm to 4 mm. The material of the balloon 52 is not specifically restricted so long as it is flexible, and is composed, for example, of one or more of polyamides and polyamide elastomers. The surface of the balloon 52 preferably has a smooth surface, but it may not necessarily be smooth. The surface of the balloon 52 may have minute (extremely small) pores that do not penetrate the film, but may not necessarily have minute pores.

Where the balloon catheter 50 is used in such a manner that the elongated shaft 51 thereof is inserted into a body organ and the balloon 52 provided on the distal side thereof is inflated at a lesion part, it is possible to push open the lesion part and thereby to perform a treatment. The shaft 51 is provided, at a position near the distal side, with the opening portion 55 through which to introduce the guide wire 57. In other words, this balloon catheter 50 is a so-called rapid exchange type catheter.

Figure 2:
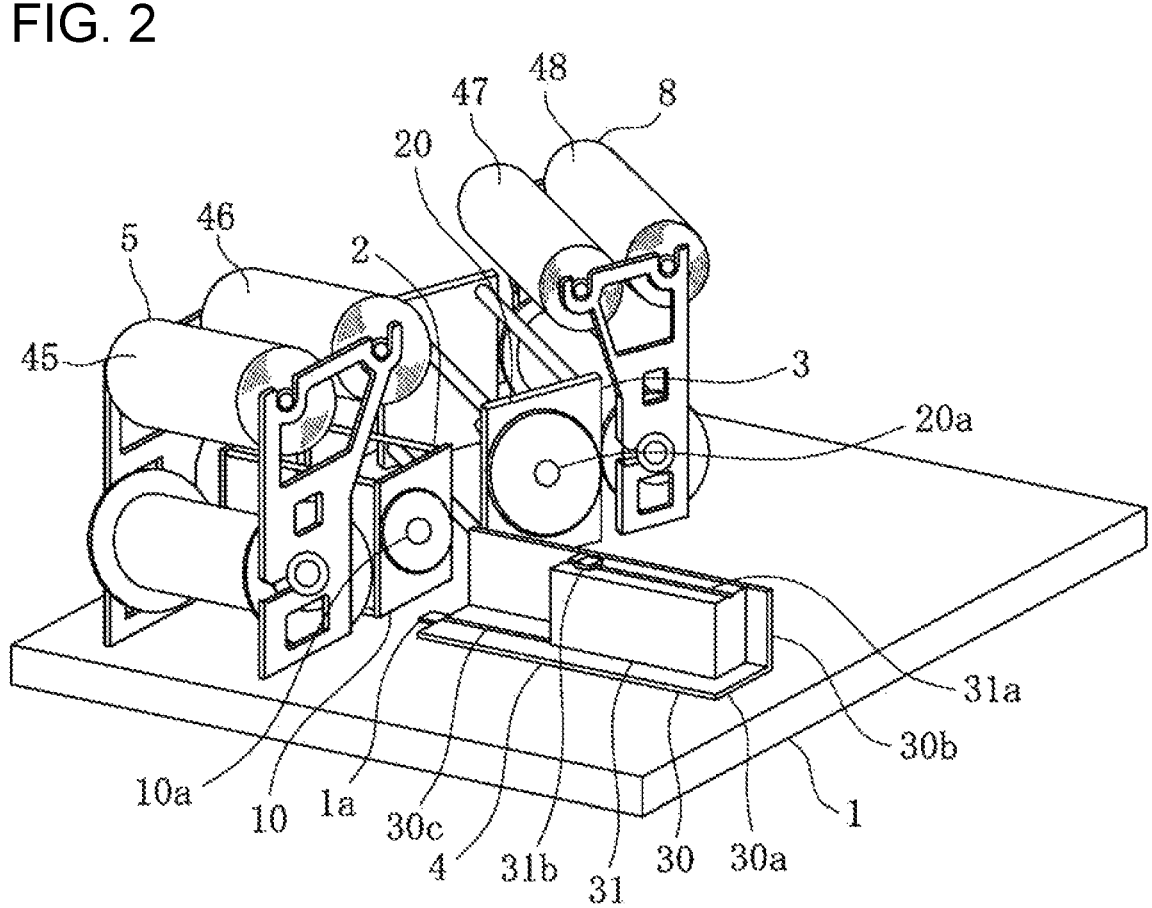
FIG. 2 is a perspective view of a balloon wrapping apparatus.

In the next place, the balloon wrapping apparatus will be described. As depicted in FIG. 2, the balloon wrapping apparatus has a pleating section 2, a folding section 3 and a support base 4 disposed on a base 1 formed in a base shape. The pleating section 2 is capable of forming the balloon 52 with wing shapes. The folding section 3 is capable of folding the wing shapes formed in the balloon 52 in the manner of being wrapped around the inner tube 54 of the shaft 51. The support base 4 is capable of disposing and holding the balloon catheter 50 thereon. The wing shapes formed in the balloon 52 are formed of pleats of balloon thin film material having a length extending substantially in a major axis direction of the balloon 52, and are so formed that the pleats project in the circumferential direction from the major axis of the balloon 52, as viewed in a section perpendicular to the major axis of the balloon 52. In accordance with an exemplary embodiment, the length of the wing shapes in the major axis direction does not exceed the length of the balloon 52, and is, for example, approximately 3 mm to 400 mm, preferably approximately 3 mm to 300 mm, more preferably approximately 30 mm to 300 mm, and further preferably approximately 40 mm to 200 mm. The length by which the wing shape projects in the circumferential direction from the shaft 51 can be, for example, 1 mm to 8 mm. The number of the wing shapes is not particularly limited, and can be selected from among two, three, four, five, six and seven. In this embodiment, three wing shapes are adopted.

A film supplying section 5 for supplying a first film 45 and a second film 46 to the pleating section 2 is disposed on the base 1, adjacently to the pleating section 2. In addition, a film supplying section 8 is disposed on the base 1, adjacently to the folding section 3, whereby a first film 47 and a second film 48 can be supplied to the folding section 3.

The pleating section 2 has a front surface plate 10 perpendicular to the base 1, and the front surface plate 10 has an insertion hole 10*a* through which a distal portion of the balloon catheter 50 can be inserted. In addition, the folding section 3 has a front surface plate 20 perpendicular to the base 1, and the front surface plate 20 has an insertion hole 20*a* through which the distal portion of the balloon catheter 50 can be inserted. The front surface plate 20 of the folding section 3 is oriented in a direction different by a predetermined angle from a direction in which the front surface plate 10 of the pleating section 2 is oriented.

A positioning section 1*a* capable of positioning the support base 4 to be oriented in two directions is disposed on the base 1. In FIG. 2, the support base 4 is positioned by the positioning section 1*a* in such a manner as to face the front surface plate 10 of the pleating section 2. According to the positioning section 1*a*, the support base 4 can also be positioned in such a manner as to face the front surface plate 20 of the folding section 3.

The support base 4 can include a base section 30 placed on the base 1, and a holding base section 31 which can be moved horizontally on the base section 30. The base section 30 can include a bottom surface portion 30*a* placed on an upper surface of the base 1 and positioned by the positioning section 1*a*, and a side surface portion 30*b* extending vertically upward from a side portion of the bottom surface portion 30*a*. A slide guide portion 30*c* for guiding the holding base section 31 is formed at an upper surface of the bottom surface portion 30*a*.

In accordance with an exemplary embodiment, the holding base section 31 is formed substantially in the shape of a rectangular parallelepiped which makes contact with the bottom surface portion 30*a* and the side surface portion 30*b* of the base section 30, and its lower surface is slidably guided by the slide guide portion 30*c* of the bottom surface portion 30*a*. An upper surface of the holding base section 31 has a groove-shaped placing portion 31*a* on which the shaft 51 of the balloon catheter 50 can be placed. In accordance with an exemplary embodiment, the holding base section 31 is provided with a holding portion 31*b* such as to cover from above a part of the placing portion 31*a*. The holding portion 31*b* is capable of holding and fixing the shaft 51 of the balloon catheter 50 placed on the placing portion 31*a*.

In a state in which the support base 4 faces the front surface plate 10 of the pleating section 2, the center of the insertion hole 10*a* formed in the front surface plate 10 is located on an extension line of the placing portion 31*a* of the holding base section 31. Therefore, the balloon catheter 50 having the shaft 51 placed on the placing portion 31*a* is inserted into the pleating section 2 through the center position of the insertion hole 10*a*. In a state in which the support base 4 faces the front surface plate 20 of the folding section 3, the center of the insertion hole 20*a* formed in the front surface plate 20 is located on an extension line of the placing portion 31*a* of the holding base section 31. That is, the balloon catheter 50 having the shaft 51 placed on the placing portion 31*a* is inserted into the folding section 3 through the center position of the insertion hole 20*a*.

Now, the structure of the pleating section 2 will be described below. As illustrated in FIG. 3, the pleating section 2 is provided therein with three blades 12. Each of the blades 12 is a plate-shaped member which is the same in sectional shape at each position along the axial direction of the balloon catheter 50 inserted. The blades 12 can be disposed such that they are, for example, at an angle of 120° from one another, with the center position in regard of insertion of the balloon 52 as a reference. In other words, the blades 12 are disposed at regular angular intervals along the circumferential direction. The blade 12 has a rotational center portion 12a near an outer circumferential end portion thereof, and can be moved rotationally about the rotational center portion 12a. In addition, the blade 12 has a moving pin 12d extending in the axial direction, on the inner circumferential side of the rotational center portion 12a. The moving pin 12d is fitted in a fitting groove 14a formed in a rotary member 14 which is rotatable in the pleating section 2. The rotary member 14 is interlocked with a beam portion 16 extending substantially horizontally. The rotary member 14 is rotatable by receiving a rotating force from the beam portion 16 which is inclined by receiving a force from a drive source 15 such as a hydraulic cylinder or a motor. When the rotary member 14 is rotated, the moving pins 12d fitted in the fitting grooves 14a are moved in the circumferential direction, whereby each of the blades 12 is moved rotationally about the rotational center portion 12a. With the three blades 12 moved rotationally, a space region in a central area surrounded by the blades 12 can be narrowed.

The blade 12 has a first shape forming portion 12b and a second shape forming portion 12c which are substantially arcuate in shape, at inner circumferential end portions on the side opposite to the rotational center portion 12a. Attendant on rotary movement of the blade 12, the first shape forming portion 12b makes contact with the surface of the balloon 52 inserted in the pleating section 2, whereby the balloon 52 can be formed with wing shapes. Attendant on rotary movement of the blade 12, the second shape forming portion 12c makes contact with the wing portion formed in the balloon 52, whereby the wing shape can be curved in a predetermined direction. In addition, the pleating section 2 has a heater (not depicted) for heating the blades 12. Note that the blades 12 may have a function of cooling.

The blades 12 are supplied with the first film 45 and the second film 46 which are formed of resin, from the film supplying section 5. For guiding each of the films, a plurality of rotary shaft portions 13 are provided in the pleating section 2. The first film 45 is supplied from a first film holding section 40 and through the rotary shaft portion 13 to be fed to a surface of the blade 12 disposed at an upper part. In addition, the first film 45 is fed through the blade 12 and the rotary shaft portion 13 to reach a film take-up section 42. The second film 46 is supplied from a second film holding section 41 and through the rotary shaft portion 13 to be fed to the two blades 12 disposed at lower parts. In addition, the second film 46 is fed through the rotary shaft portion 13 to reach the film take-up section 42. As a result of these, a center position of the pleating section 2 in which the balloon 52 is inserted is in the state of being surrounded by the first film 45 and the second film 46.

The first film 45 and the second film 46 have a protecting function for preventing direct contact of the balloon 52 with the surfaces of the blades 12 when the balloon 52 is inserted into the pleating section 2 and the blades 12 are moved rotationally to form the balloon 52 with wing shapes. After the wing shapes of the balloon 52 are formed, predetermined lengths of the first film 45 and the second film 46 are taken up by the film take-up section 42. In other words, the portions of the first film 45 and the second film 46 which portions have once made contact with the balloon 52 do not make contact with the balloon 52 again, and new portions of the films are supplied to the center position of the pleating section 2 every time the balloon 52 is inserted.

Next, the structures of the distal portion of the shaft 51 and the balloon 52 will be described below. As illustrated in FIG. 4, the shaft 51 includes a hollow outer tube 53 and a hollow inner tube 54. The inner tube 54 is accommodated in the hollow inside of the outer tube 53, and the shaft 51 has a double-tube structure at its distal portion. The hollow inside of the inner tube 54 forms a guide wire lumen 58 in and through which a guide wire 57 is to be inserted and passed. In addition, an inflation lumen 59 through which an inflation fluid for the balloon 52 is permitted to flow is formed in the hollow inside of the outer tube 53 and on the outside of the inner tube 54. The inner tube 54 is open to the exterior at an opening portion 55.

In accordance with an exemplary embodiment, the inner tube 54 protrudes to the distal side beyond a distal end of the outer tube 53. The balloon 52 has a proximal-side end portion fixed to a distal portion of the outer tube 53, and has a distal-side end portion fixed to a distal portion of the inner tube 54. As a result of this, the inside of the balloon 52 communicates with the inflation lumen 59. The balloon 52 can be inflated by injecting an inflation fluid into the balloon 52 through the inflation lumen 59. The inflation fluid may be either a gas or a liquid; for example, a gas such as helium gas, $CO_2$ gas and $O_2$ gas or a liquid such as a saline solution and a contrast medium can be used as the inflation fluid.

The outer tube 53 and the inner tube 54 are preferably formed from a material that has a certain degree of flexibility. Examples of such a material include polyolefins such as polyethylene, polypropylene, polybutene, ethylene-propylene copolymer, ethylene-vinyl acetate copolymer, ionomers, or mixtures of two or more of them, flexible polyvinyl chloride resin, polyamides, polyamide elastomers, polyesters, polyester elastomers, polyurethane, fluoro-resin such as polytetrafluoroethylene, silicone rubbers, and latex rubbers.

As depicted in FIG. 4, of the balloon catheter 50 inserted in the pleating section 2, the shaft 51 is placed on the placing portion 31a of the support base 4 and is held and fixed by the holding portion 31b. In this instance, the shaft 51 is disposed in such a manner that the opening portion 55 is positioned on the proximal side of the holding portion 31b. That portion of the shaft 51 which is on the distal side of the support base 4 and which includes the balloon 52 is not supported from below, but a core metal member 6 to be inserted in the guide wire lumen 58 is provided on the distal side of the opening portion 55. By the core metal member 6, bending of the shaft 51 due to its own weight is restrained.

The core metal member 6 is formed in a thin elongated wire-like shape or a hollow shape from a metallic material. As the metallic material for forming the core metal member 6, there is selected a material having such a degree of hardness that with the core metal member 6 inserted in the balloon 52 and the shaft 51, the distal portion of the shaft 51 inclusive of the balloon 52 does not bend due to its own weight. The metallic material for forming the core metal member 6 is not specifically restricted, and examples thereof include stainless steel, Ni—Ti alloys, tungsten, and hard metals. In addition, the core metal member 6 may be formed by annealing any of these metallic materials, to realize a shape memory property.

In accordance with an exemplary embodiment, the core metal member 6 is formed in a substantially circular shape in section, and its outside diameter is smaller than the inside diameter of the inner tube 54, for example, by 0.01 mm to 0.1 mm. If the outside diameter of the core metal member 6 is smaller than the aforesaid appropriate value in relation to the inside diameter of the inner tube 54, the balloon 52 part cannot be held sufficiently by the core metal member 6, and bending of the balloon 52 would occur. As a result, the shaft 51 may be distorted when the balloon 52 is formed with wing shapes by the pleating section 2. On the other hand, if the outside shape of the core metal member 6 is greater than the aforesaid appropriate value in relation to the inside diameter of the inner tube 54, the core metal member 6 may interfere with the inner surface of the inner tube 54, possibly breaking the inner tube. With the outside diameter of the core metal member 6 set as above-mentioned, these problems can be prevented from occurring.

In accordance with an exemplary embodiment, the pleating section 2 has a front surface plate 10 on the side of insertion of the balloon 52, and has a back surface plate 11 on the side opposite to the side of the front surface plate 10. The back surface plate 11 is formed with a fixing insertion portion 11a, in which a holding member 7 can be inserted and fixed. A distal portion of the core metal member 6 is fixed to the holding member 7, and the holding member 7 is fixed to the fixing insertion portion 11a of the back surface plate 11, so that the core metal member 6 is in a state in which its distal portion is held by the pleating section 2.

The core metal member 6 has such a length as to extend from the distal side of the distal end of the balloon 52 to the proximal side of the opening portion 55 of the shaft 51. Since the opening portion 55 is located on the proximal side of the holding portion 31b of the support base 4, the core metal member 6 is also held by the holding portion 31b at the position where the shaft 51 is held by the holding portion 31b. In other words, the core metal member 6 is held by the holding member 7 on the distal side and is held by the holding portion 31b of the support base 4 on the proximal side, whereby bending of the shaft 51 due to its own weight can be restrained effectively.

In this way, by the core metal member 6, the shaft 51 is restrained from bending due to its own weight, in regard of the distal side of its part supported by the support base 4. As a result of this, the balloon 52 can be accurately positioned and inserted in relation to the pleating section 2. With the balloon 52 accurately positioned and inserted in relation to the pleating section 2, the balloon 52 can be accurately formed with wing shapes, and the wing shapes can be made uniform in the circumferential direction.

Figure 5:
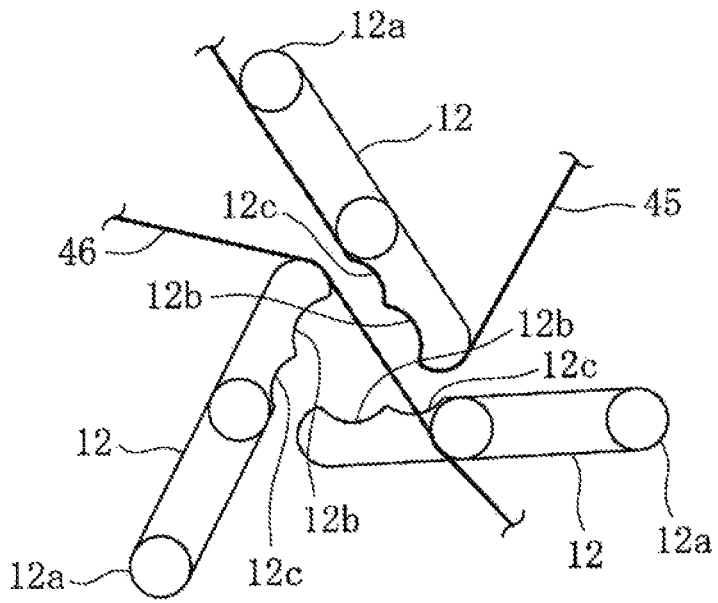
FIG. 5 is a front view of the blades in the pleating section.

The pleating of the balloon 52 in the pleating section 2 will be described further. As depicted in FIG. 5, in a state before insertion of the balloon 52, the first shape forming portions 12b and the second shape forming portions 12c of the three blades 12 are in the state of being spaced from one another. A central region between the blades 12 is surrounded by the substantially arcuate first shape forming portions 12b, and the balloon 52 yet to be wrapped can be inserted therein.

In forming the balloon 52 with wing shapes, first, the shaft 51 of the balloon catheter 50 is mounted to the support base 4. The inflation fluid is injected into the balloon 52 through the hub 56 and the inner tube 54, whereby the balloon 52 is put into a state of being inflated to a certain extent. In addition, the blades 12 of the pleating section 2 are heated. In this condition, the balloon 52 is inserted into the pleating section 2, and the blades 12 are moved rotationally, whereby wing shapes are formed.

Figure 6:
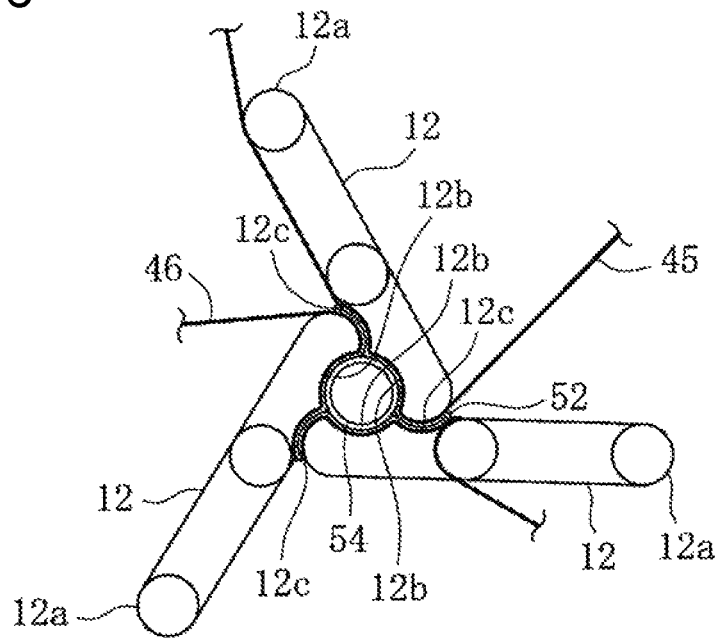
FIG. 6 is a front view of the blades in a state in which the blades are moved rotationally from the state of FIG. 5 to form the balloon with wing shapes.

As illustrated in FIG. 6, when the blades 12 are moved rotationally, the first shape forming portions 12b of the blades 12 come closer to one another, and the central region between the blades 12 is narrowed. Attendant on this, the balloon 52 inserted in the central region between the blades 12 is pressed against the inner tube 54 by the first shape forming portions 12b. A portion of the balloon 52 which portion is not pressed by the first shape forming portion 12b is pushed out into a gap between a distal portion of one blade 12 and the second shape forming portion 12c of the blade 12 adjacent to the one blade 12, whereby a wing shape curved to one side is formed. Since the balloon 52 is heated by the blades 12, the wing shapes thus formed can be maintained in their shape. In this way, the balloon 52 is formed with three wing shapes in the circumferential direction.

In this instance, surfaces of the blades 12 which surfaces make contact with the balloon 52 are covered with the first film 45 and the second film 46, so that the balloon 52 does not make direct contact with the surfaces of the blades 12. If the balloon 52 is formed with the wing shapes, the blades 12 are moved rotationally in the manner of being returned into their original positions, and the balloon 52 is withdrawn from the pleating section 2. Note that in the process of pleating, a step of excessively inflating the balloon 52 and then deflating the balloon 52 a little or a step of inflating the balloon 52 while avoiding excessive inflation and then deflating the balloon 52 a little may be provided.

Figure 7:
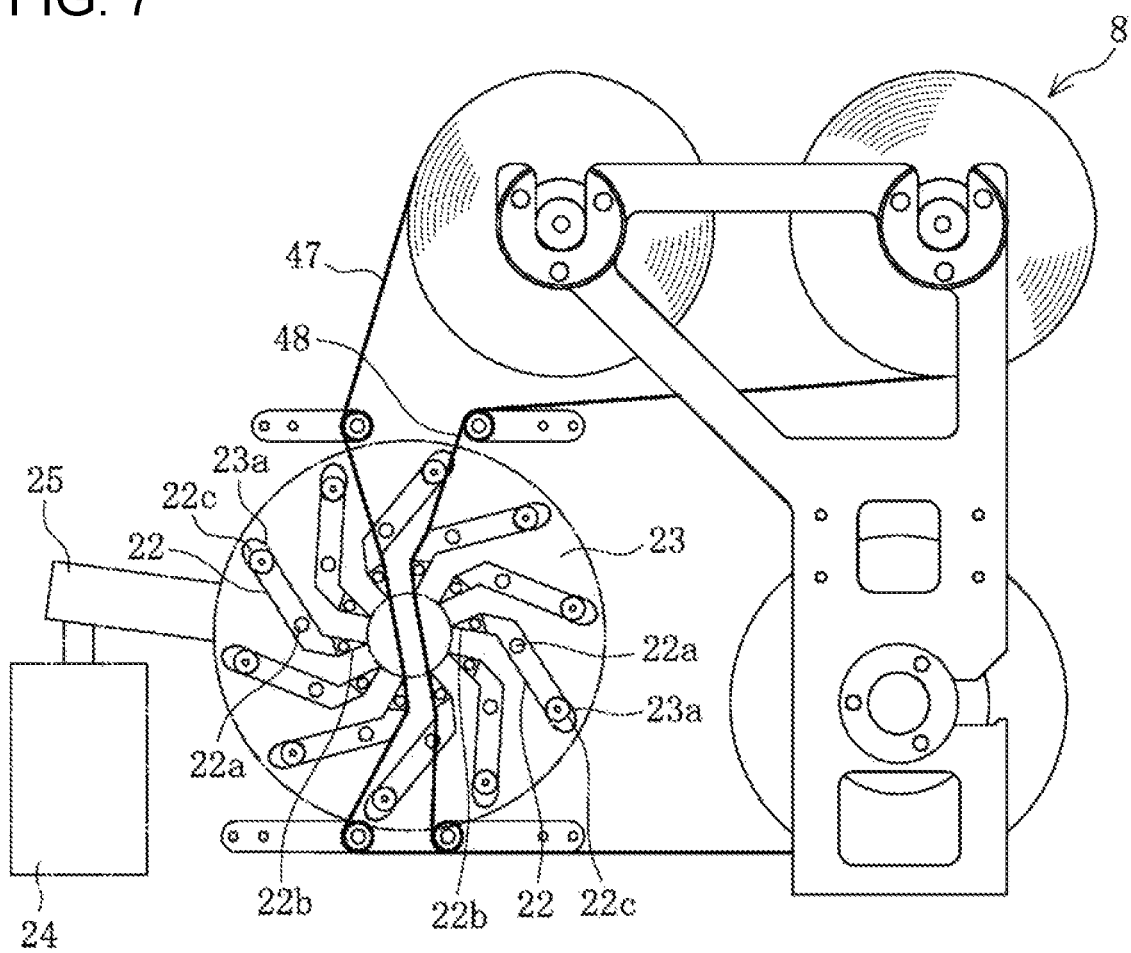
FIG. 7 is a front view representing a layout of blades and a film supplying section in a folding section.

Now, the structure of the folding section 3 will be described below. As illustrated in FIG. 7, the folding section 3 is provided therein with ten blades 22. Each of the blades 22 can be a plate-shaped member formed to be the same in sectional shape at each position along the axial direction of the balloon catheter 50 to be inserted. In accordance with an exemplary embodiment, the blades 22 can be disposed such that they are, for example, at an angle of 36° from one another, with the center position in regard of insertion of the balloon as a reference. In other words, the blades 22 are disposed at regular angular intervals along the circumferential direction. The blade 22 has a rotational center portion 22a near an outer circumferential end portion thereof, and can be moved rotationally about the rotational center portion 22a. In addition, the blade 22 has a moving pin 22c extending in the axial direction, near a substantially outer circumferential end portion thereof. The moving pin 22c is fitted in a fitting groove 23a formed in a rotary member 23 which is rotatable in the folding section 3. The rotary member 23 is interlocked with a beam portion 25 extending substantially horizontally. The rotary member 23 is rotatable by receiving a rotating force from the beam portion 25 which is inclined by receiving a force from a drive source 24 such as a hydraulic cylinder or a motor. When the rotary member 23 is rotated, the moving pins 22c fitted in the fitting grooves 23a are moved in the circumferential direction, whereby each of the blades 22 is moved rotationally about the rotational center portion 22a. With the ten blades 22 moved rotationally, a space region in a central area surrounded by the blades 22 can be narrowed.

The blade 22 is bent on the tip side, and has a distal portion 22b in a pointing (or pointed) shape. Attendant on rotation of the blade 22, the distal portion 22b makes contact with a surface of the balloon 52 inserted in the folding section 3, whereby the wing shapes formed in the balloon 52 can be folded in the manner of being wrapped around the inner tube 54. In addition, the folding section 3 has a heater (not depicted) for heating the blades 22. Note that the blades 22 may have a function of cooling.

In accordance with an exemplary embodiment, the blades 22 are supplied with the first film 47 and the second film 48 from the film supplying section 8. The supplying structure of each film is the same as in the case of the pleating section 2. The first film 47 and the second film 48 are disposed opposite to each other in such a manner as to sandwich a central space region surrounded by the blades 22. By the first film 47 and the second film 48, the balloon 52 inserted in the folding section 3 can be prevented from making direct contact with the surfaces of the blades 22.

Figure 8:
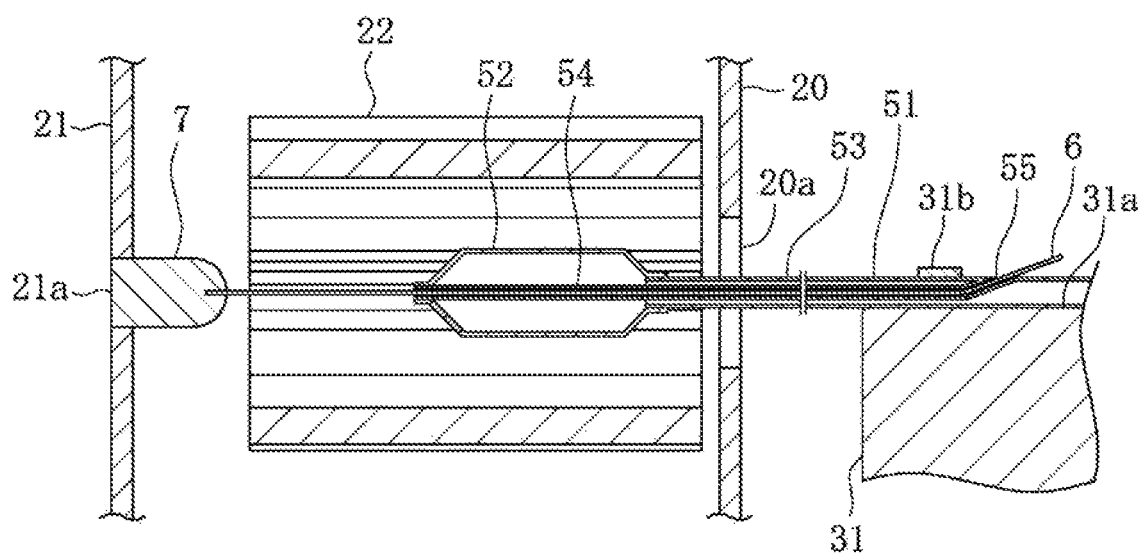
FIG. 8 is a sectional view of the balloon catheter and the folding section in a state in which the balloon is inserted in the folding section.

The balloon catheter 50 is inserted into the folding section 3 after being inserted into the pleating section 2, as aforementioned. Therefore, as depicted in FIG. 8, in the balloon catheter 50 inserted in the folding section 3, the shaft 51 is in the state of being held by the holding portion 31b of the support base 4. The core metal member 6 is also inserted in the balloon, like in the case of insertion into the pleating section 2. In addition, a distal portion of the core metal member 6 is fixed to the holding member 7, and the holding member 7 is fixed to a fixing insertion portion 21a possessed by a back surface plate 21 of the folding section 3.

In this way, also at the time of insertion into the folding section 3, the core metal member 6 is in the state of being inserted in the balloon 52, whereby bending of the shaft 51 due to its own weight is restrained, and the balloon 52 can be accurately positioned and inserted into the center position of the folding section 3. With the balloon 52 accurately positioned and inserted in relation to the folding section 3, generation of back folding at the time of folding the balloon 52 can be restrained.

Figure 9:
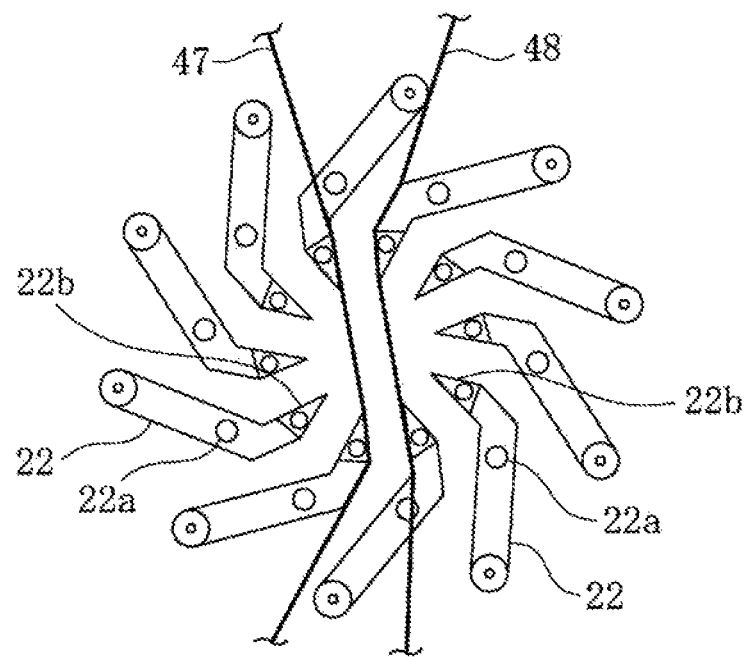
FIG. 9 is a front view of the blades in the folding section.

The folding of the balloon 52 in the folding section 3 will be described further. As depicted in FIG. 9, in a state before insertion of the balloon 52, the distal portions 22b of the blades 22 are in the state of being spaced from one another in the circumferential direction. The balloon 52 formed with the wing shapes can be inserted into a central region which is surrounded by the blades 22 and which is between the first film 47 and the second film 48.

Figure 10:
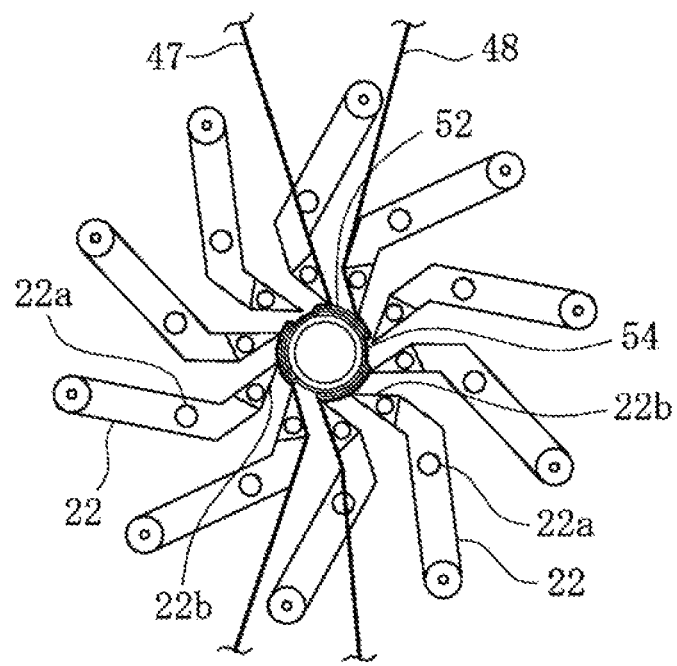
FIG. 10 is a front view of the blades in a state in which the blades are moved rotationally from the state of FIG. 9 to fold the wing shapes of the balloon.

When the blades 22 are moved rotationally, the distal portions 22b of the blades 22 come closer to one another, and the central region between the blades 22 is narrowed, as depicted in FIG. 10. Attendant on this, the balloon 52 inserted in the central region between the blades 22 is put into a state in which the wing shapes are laid flat in the circumferential direction by the distal portions 22b of the blades 22. Since the blades 22 are preliminarily heated before insertion of the balloon 52 and the balloon 52 is heated by the blades 22, the wing shapes laid flat in the circumferential direction by the blades 22 can be maintained in their shape. Note that the blades 22 may not be heated, or may be cooled.

In this instance, the surfaces of the blades 22 which surfaces make contact with the balloon 52 are covered with the first film 47 and the second film 48, so that the balloon 52 does not make direct contact with the surfaces of the blades 22. After the wing shapes of the balloon 52 are folded, the blades 22 are moved rotationally in the manner of being returned to their original positions, and the balloon 52 is withdrawn from the folding section 3.

While a case in which the balloon 52 of a rapid exchange type catheter is wrapped by the balloon wrapping apparatus has been described hereinabove, a balloon 62 of an over-the-wire type catheter can also be wrapped by the same balloon wrapping apparatus.

Figure 11:
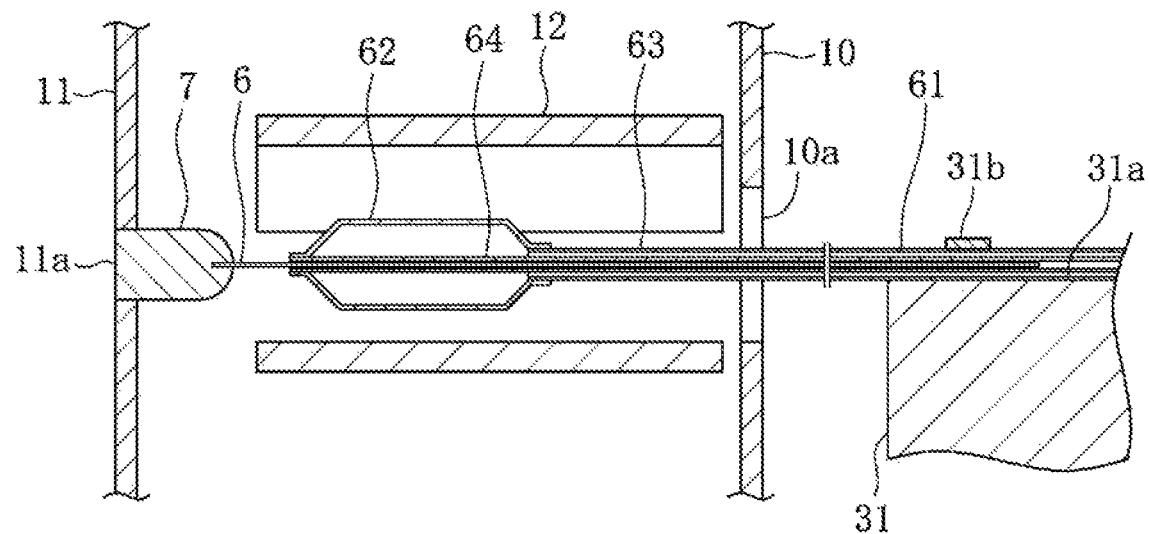
FIG. 11 is a sectional view of the balloon catheter and the pleating section in a state in which a balloon is inserted in the pleating section, in an over-the-wire type balloon catheter.

As illustrated in FIG. 11, this over-the-wire type balloon catheter 60 has the balloon 62 at a distal-side end portion of a shaft 61. The shaft 61 has an inner tube 64 disposed in a hollow inside of an outer tube 63, over the entire length on the proximal side of the balloon 62, and the outer tube 63 and the inner tube 64 extend to a hub (not depicted) provided at a proximal-side end portion of the shaft 61. The structure of the part of the balloon 62 is the same as in the case of the rapid exchange type.

In FIG. 11, the balloon 62 is in the state of being inserted in the pleating section 2, and the core metal member 6 is inserted in the balloon 62. The core metal member 6 has a distal portion fixed in relation to the holding member 7, and the holding member 7 is fixed to a fixing insertion portion 11a formed in a back surface plate 11 of the pleating section 2. In accordance with an exemplary embodiment, the core metal member 6 has a length of not less than twice the length of the balloon 62, and its proximal-side end portion is disposed in the inner tube 64. The position of a proximal end of the core metal member 6 is on the proximal side of a holding portion 31b at which the support base 4 holds the shaft 61, and the core metal member 6 has both its ends held by the holding member 7 and the holding portion 31b of the support base 4.

With the core metal member 6 thus inserted in a distal portion of the shaft 61, the shaft 61 is restrained from bending due to its own weight, in regard of the distal side of its part supported by the support base 4. As a result of this, the balloon 62 can be accurately positioned and inserted into the center positions of the pleating section 2 and the folding section 3, so that the balloon 62 can be formed with wing shapes uniform in the circumferential direction, and generation of back folding at the time of folding the wing shapes can be restrained.

Figure 12:
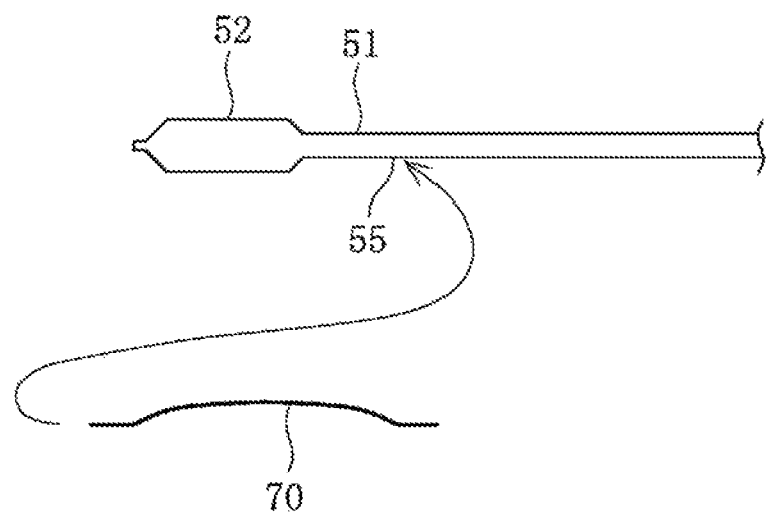
FIG. 12 is a front view of a core metal member and a balloon catheter in a second mode.

Now, a core metal member 70 in a second mode will be described below. As illustrated in FIG. 12, the core metal member 70 in the present mode is formed to have an intermediate portion curved. In FIG. 12, the core metal member 70 is inserted into a rapid exchange type balloon catheter 50 illustrated on the upper side thereof. The core metal member 70 is curved such that when it is inserted in the balloon catheter 50, its portion located in the shaft 51 is projected to the upper side.

Figure 13:
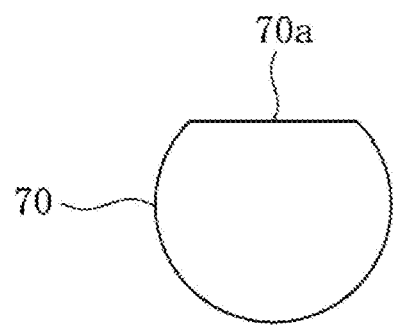
FIG. 13 is a figure representing a sectional shape of a distal portion of the core metal member in the second mode.

As illustrated in FIG. 13, at least a distal portion of the core metal member 70 has a flat surface portion 70a at a part of a circumferential surface thereof. In accordance with an exemplary embodiment, the core metal member 70 in the present mode has a distal portion fixed to the holding member 7, like in the aforementioned embodiment. The holding member 7 is provided, at its part to which the core metal member 70 is fixed, with a flat surface portion corresponding to the flat surface portion 70a, so that the core metal member 70 can be fixed in only a predetermined direction relative to the holding member 7. As a result of this, the core metal member 70 inserted in the shaft 51 can be set in a predetermined orientation, namely, in such an orientation that its curved portion is projected to the upper side.

In accordance with an exemplary embodiment, the core metal member 70 has a curve corresponding to the amount of bending of the distal portion of the shaft 51 due to its own weight. Therefore, in the state in which the core metal member 70 is inserted in the shaft 51, the bending of the shaft 51 due to its own weight and the upward curving of the core metal member 70 cancel each other, so that the shaft 51 can be set in a more horizontal state.

In this way, with a curve provided in that part of the core metal member 70 which is inserted in the shaft 51, bending of the shaft 51 due to its own weight can be restrained more securely, and an effect to form the wing shapes uniform in the circumferential direction in the pleating section 2 and an effect to restrain back folding from occurring in the folding section 3 can be enhanced. Note that setting the core metal member in a curved shape is not limited to the case of the rapid exchange type balloon catheter 50, and may be applied to the over-the-wire type balloon catheter 60.

Figure 14A:
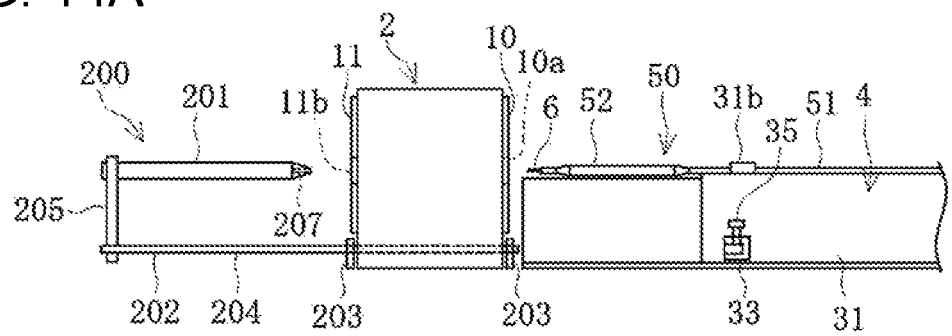
FIGS. 14A-14C are sides view depicting a pleating section in a third mode.

Now, a pleating section 2 according to a third mode will be described below. As illustrated in FIG. 14A, the pleating section 2 according to the third mode is provided with an insertion assisting section 200 for assisting the insertion of the balloon catheter 50 into the insertion hole 10*a*. The insertion assisting section 200 can be interlocked with the holding base section 31 that holds the shaft 51 of the balloon catheter 50. The insertion assisting section 200 can include an elongated assisting shaft 201, an interlock portion 202 for interlocking the assisting shaft 201 and the holding base section 31, and a support portion 203 for supporting the interlock portion 202 in a slidable manner. The interlock portion 202 can include an elongated interlock shaft 204, and a fixing portion 205 for fixing the assisting shaft 201 and the interlock shaft 204.

One end of the interlock shaft 204 is fixed to the assisting shaft 201 by the fixing portion 205. The other end of the interlock shaft 204 abuts on, and is interlockable with, a holding base side interlock portion 33 of the holding base section 31. The holding base side interlock portion 33 has, for example, a fixing screw 35 for fixing the assisting shaft 201.

In accordance with an exemplary embodiment, the assisting shaft 201 is formed at a distal portion thereof with a cavity portion 207 into which the core metal member 6 to be inserted in the balloon catheter 50 can be inserted. With the core metal member 6 inserted in the cavity portion 207, the balloon catheter 50 can be restrained from bending. Note that the assisting shaft 201 can also hold the shaft 51 of the balloon catheter 50. The assisting shaft 201 can enter a back surface hole 11*b* provided in the pleating section 2 on the side opposite to the insertion hole 10*a*, and can protrude from the insertion hole 10*a* to the exterior.

Figure 14B:
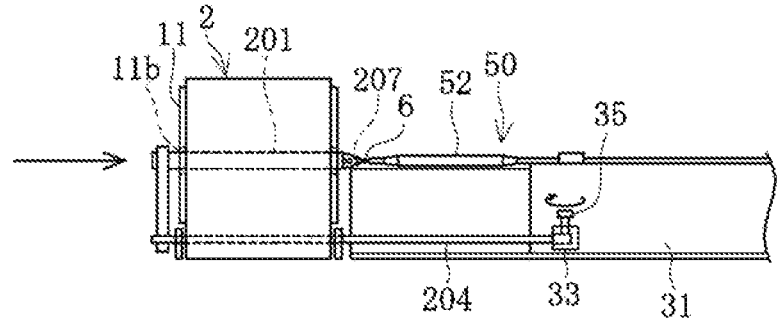
Figure 14C:
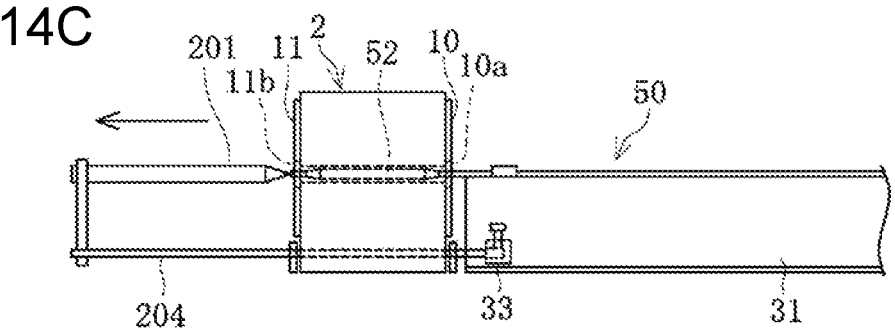

In inserting the balloon catheter 50 into the pleating section 2, the assisting shaft 201 is inserted into the back surface hole 11*b* of the pleating section 2 and is protruded from the insertion hole 10*a*, as depicted in FIG. 14B. Next, the core metal member 6 is inserted into the cavity portion 207 of the assisting shaft 201, and the interlock shaft 204 is fixed to the holding base section 31. Thereafter, as depicted in FIG. 14C, the holding base section 31 is moved toward the pleating section 2, whereon the balloon catheter 50 is inserted through the insertion hole 10*a* into the inside of the pleating section 2. In this instance, the assisting shaft 201 is also moved together with the holding base section 31, and, therefore, the balloon 52 can be inserted into a central area of the blades 12 of the pleating section 2 while a state of the balloon 52 being held by the assisting shaft 201 is maintained. As a result of this, the balloon 52 can be accurately positioned, and inserted, in relation to the pleating section 2. Note that the insertion assisting section 200 may be provided in the folding section 3.

In addition, the aforementioned assisting shaft may be provided with a mechanism for clamping and fixing the core metal member 6. The mechanism for clamping and fixing the core metal member 6 is, for example, a collet chuck, a scroll chuck, a drill chuck, or an independent chuck. In addition, the support base for holding the balloon catheter 50 may have such a structure that the balloon catheter 50 can be rotated about its axis, in the state of being held on the support base. In this case, with the balloon catheter 50 rotated in a direction reverse to the folding direction at the time of folding the wing shapes of the balloon 52 in the folding section 3, the effect to restrain back folding can be enhanced.

EXAMPLES

Examples of the present invention will be described below. Drug-coated balloons of Examples 1 to 13 were produced under the conditions set forth in Table 1, Table 2, and Table 3 (FIGS. 15-17).

Example 1

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock (valve) was attached to a hub portion of a balloon catheter (material of balloon: nylon, the surface being smooth and non-porous) 2.0 mm in diameter and 40 mm in length when inflated, the balloon was inflated at 4 atm, and coating with the coating liquid was slowly conducted such that the amount of paclitaxel on the balloon would be approximately 3.2 µg/mm$^2$. After the coating, the balloon catheter was dried, to produce a drug-coated balloon.

(2) Step of Pleating the Drug-Coated Balloon

A core metal member (material: SUS) in the form of wire (solid) 0.39 mm in diameter and 700 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to a holding base section by a holding portion fitted with silicone rubber. In this instance, the three-way cock of the hub of the balloon catheter was attached to an air injection and suction mechanism for inflating and deflating the balloon of the wrapping apparatus. The core metal member protruding from a distal portion of the balloon catheter was inserted into a distal support (assisting shaft) of a pleating section 2. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The ten blades were held in a closed state for a while, after which the blades were slowly opened, to spread the first film and the second film. Thereafter, the balloon was drawn back from the folding section.

Example 2

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 4.0 mm in diameter and 200 mm in length when inflated, the balloon was inflated at 4 atm, and coating with the coating liquid was slowly conducted such that the amount of paclitaxel on the balloon would be approximately 3.6 μg/mm$^2$. After the coating, the balloon catheter was dried, to produce a drug-coated balloon.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 3

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 3.0 mm in diameter and 200 mm in length when inflated, the balloon was inflated at 4 atm, and coating with the coating liquid was slowly conducted such that the amount of paclitaxel on the balloon would be approximately 3.6 μg/mm$^2$. After the coating, the balloon catheter was dried, to produce a drug-coated balloon.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock (valve) of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 4

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock (valve) was attached to a hub portion of a balloon catheter (material of balloon: nylon, the surface being smooth and non-porous) 2.0 mm in diameter and 200 mm in length when inflated, the balloon was inflated at 4 atm, and coating with the coating liquid was slowly conducted such that the amount of paclitaxel on the balloon would be approximately 3.2 µg/mm². After the coating, the balloon catheter was dried, to produce a drug-coated balloon.

(2) Step of Pleating the Drug-Coated Balloon

A core metal member (material: SUS) in the form of wire 0.38 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The ten blades were held in a closed state for a while, after which the blades were slowly opened, to spread the first film and the second film. Thereafter, the balloon was drawn back from the folding section.

Example 5

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock (valve) was attached to a hub portion of a balloon catheter (material of balloon: nylon, the surface being smooth and non-porous) 6.0 mm in diameter and 200 mm in length when inflated, the balloon was inflated at 4 atm, and coating with the coating liquid was slowly conducted such that the amount of paclitaxel on the balloon would be approximately 3.2 µg/mm². After the coating, the balloon catheter was dried, to produce a drug-coated balloon.

(2) Step of Pleating the Drug-Coated Balloon

A core metal member (material: SUS) in the form of wire 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 6

(1) Production of Drug-Coated Balloon

In the same procedure as in the production example of the drug-coated balloon in Example 1, a drug-coated balloon of a balloon catheter (material of balloon: nylon, the surface being smooth and non-porous) 6.0 mm in diameter and 200 mm in length was produced.

(2) Step of Pleating the Drug-Coated Balloon

A core metal member (material: SUS) in the form of wire 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock (valve) of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the distal support was fixed. Subsequently, the support base section with the shaft of the balloon catheter fixed thereto was pulled backward by 5 mm and was fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, a collet chuck affixed to a distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having eight blades. After the balloon was pushed in completely, the position of the distal support was fixed, and the support base section with the shaft of the balloon catheter fixed thereto was pulled backward by 5 mm and was fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The eight blades were held in a closed state for a while, after which the blades were slowly opened, to spread the first film and the second film, and the balloon was drawn back from the folding section.

Example 7

(1) Production of Drug-Coated Balloon

In the same procedure as in the production example of the drug-coated balloon in Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock (valve) of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the support base section with the shaft of the balloon catheter fixed thereto was fixed. Subsequently, the distal support was pulled forward by 5 mm, and was then fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the support base section with the shaft of the balloon catheter fixed thereto was fixed. Subsequently, the distal support was pulled forward by 5 mm and was then fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the first films, and the balloon was drawn back from the folding section.

Example 8

(1) Production of Drug-Coated Balloon

In the same procedure as in the production example of the drug-coated balloon in Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock (valve) of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the distal support was fixed. Subsequently, the support base section with the shaft of the balloon catheter fixed thereto was pulled backward with a force of 5 N, and was then fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the distal support was fixed, and the support base section with the shaft of the balloon catheter fixed thereto was pulled backward by a force of 5 N and was fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the films, and the balloon was drawn back from the folding section.

Example 9

(1) Production of Drug-Coated Balloon

In the same procedure as in the production example of the drug-coated balloon in Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock (valve) of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the support base section with the shaft of the balloon catheter fixed thereto was fixed. Subsequently, the distal support was pulled forward with a force of 1 N, and was then fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the support base section with the shaft of the balloon catheter fixed thereto was fixed. Subsequently, the distal support was pulled forward with a force of 1 N, and was then fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the films, and the balloon was drawn back from the folding section.

Example 10

(1) Production of Drug-Coated Balloon

In the same procedure as in the production example of the drug-coated balloon in Example 1, a drug-coated balloon of a balloon catheter (material of balloon: nylon, the surface being smooth and non-porous) 3.0 mm in diameter and 20 mm in length was produced.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way cock (valve) of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the first film and the second film. Thereafter, the balloon was drawn back from the folding section.

Example 11

(1) Production of Drug-Coated Balloon

In the same procedure as in the production example of the drug-coated balloon in Example 1, a drug coated balloon of a balloon catheter (material of balloon: nylon, the surface being smooth and non-porous) 4.0 mm in diameter and 200 mm in length was produced. Coating was conducted such that the amount of paclitaxel on the balloon would be approximately 3.6 µg/mm$^2$.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between the blades of the pleating section having three blades. Note that the pleating section was not provided with films. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between the blades of the folding section having ten blades. Note that the pleating section was not provided with films. After the balloon was pushed in completely, the heated blades were slowly closed. The ten blades were held in a closed state for a while, after which the blades were slowly opened, and the balloon was drawn back from the folding section.

Example 12

(1) Production of Drug-Coated Balloon

In the same procedure as in the production example of the drug-coated balloon in Example 1, a drug-coated balloon of a balloon catheter (material of balloon: nylon, the surface being smooth and non-porous) 3.0 mm in diameter and 200 mm in length was produced. Coating was conducted such that the amount of paclitaxel on the balloon would be approximately 3.6 µg/mm$^2$.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way cock (valve) of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between the blades of the pleating section having three blades. Note that the pleating section was not provided with films. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between the blades of the folding section having ten blades. Note that the pleating section was not provided with films. After the balloon was pushed in completely, the heated blades were slowly closed. The ten blades were held in a closed state for a while, after which the blades were slowly opened, and the balloon was drawn back from the folding section.

Example 13

(1) Production of Drug-Coated Balloon

In the same procedure as in the production example of the drug-coated balloon in Example 1, a drug-coated balloon of a balloon catheter (material of balloon: nylon, the surface being smooth and non-porous) 2.0 mm in diameter and 200 mm in length was produced.

(2) Step of Pleating the Drug-Coated Balloon

A core metal member (material: SUS) in the form of wire 0.38 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into, and fixed to, a collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

<Measurement of Amount of Paclitaxel Remaining on Balloon after Folding>

For the drug-coated balloons produced in Examples 1 to 5 and Examples 11 and 12, the amount of paclitaxel remaining on the balloon was measured in the following procedure.

(1) Method

The drug-coated balloon after folding was immersed in a methanol solution, followed by shaking by use of a shaker for 10 minutes, to extract paclitaxel present in the coating on the balloon. The light absorbance, at 227 nm, of the methanol solution into which paclitaxel had been extracted was measured by high-speed liquid chromatography using an ultraviolet-and-visible absorptiometer, and the amount of paclitaxel per balloon ([µg/balloon]) was determined. Further, from the amount of paclitaxel thus obtained and the surface area of the balloon, the amount of paclitaxel per unit area of balloon ([µg/mm$^2$]) was calculated.

(2) Results

In Table 4 (FIG. 18), the amount of paclitaxel (theoretical value) on the balloon upon coating and the amount of paclitaxel (measured value) on the balloon after folding are depicted as amount per unit area. In addition, retention rate of paclitaxel after folding was calculated by dividing the amount of paclitaxel on the balloon after folding by the amount of paclitaxel on the balloon upon coating, and multiplying the quotient by 100.

As depicted in Table 4 (FIG. 18), in every one of Examples 1 to 5, the retention rate of paclitaxel was high. On the other hand, in Examples 11 and 12, the retention rate of paclitaxel was as low as less than 80%. Note that the films were used in the pleating and folding in Examples 1 to 5, but films were not used in the pleating and folding in Examples 11 and 12. It could be confirmed that detachment of the drug coating layer can be reduced by using films in pleating and folding. Evaluation of generation of back folding upon folding For the drug-coated balloons prepared under the conditions of Example 4 and Example 13, the generation rate of back folding upon folding was evaluated.

(1) Method

The wrapping direction of wings of the drug-coated balloons upon folding was observed on a digital microscope. In the case where the wrapping directions of the wings were not in one direction and there was the wings whose wrapping direction was reverse to the normal direction, the case was counted as back folding.

(2) Results

Table 5 (FIG. 19) depicts the number of drug-coated balloons in which back folding was generated, the total number of drug-coated balloons subjected to folding, and generation rate of back folding. The generation rate of back folding was calculated by dividing the number of drug-coated balloons in which back folding was generated by the total number of drug-coated balloons subjected to folding, and multiplying the quotient by 100.

As depicted in Table 5 (FIG. 19), in the method of Example 4 in which the balloon was rotated during folding, back folding was scarcely generated. On the other hand, in the method of Example 13 in which the balloon was not rotated during folding, back folding was generated in approximately one half of the samples subjected to folding. Accordingly, it could be confirmed that the rotation of the balloon during folding has an effect to reduce the generation of back folding.

As has been described above, the balloon wrapping apparatus according to the present embodiment is a balloon wrapping apparatus for wrapping a balloon 52 provided at a distal portion of an elongated shaft 51, and includes: the pleating section 2 that forms the balloon 52 with wing shapes; the folding section 3 that folds the wing shapes formed in the balloon 52 in the circumferential direction; the support base 4 that supports a portion other than a distal portion of the shaft 51 and makes the distal portion of the shaft 51 insertable into the pleating section 2 and the folding section 3; and the core metal member 6 to be inserted in the shaft 51, in which the core metal member 6 is inserted in the shaft 51 from a distal end position of the balloon 52 to at least the proximal side of a proximal end position of the balloon 52. As a result of this, the distal portion of the shaft 51 inclusive of the balloon 52 is supported by the core metal member 6 in such a manner as not to bend, and, therefore, the balloon 51 can be accurately positioned and inserted in relation to the pleating section 2 and the folding section 3. For this reason, the wing shapes of the balloon 52 can be formed uniformly in the circumferential direction in the pleating section 2, and back folding can be restrained from being generated at the time of folding the wing shapes in the folding section 3.

In addition, where the shaft 61 is formed to have the inner tube 64 and the outer tube 63 disposed concentrically, with the inner tube 64 extending to a proximal-side end portion of the shaft 61, and the core metal member 6 has a length of at least twice the length of the balloon 62, bending of a distal portion of the shaft 61 inclusive of the balloon 62 can be effectively restrained, in the over-the-wire type balloon catheter 60.

In addition, where the shaft 51 is formed to have the inner tube 54 and the outer tube 53 disposed concentrically, with the inner tube 54 having the opening portion 55 that opens to the outside of the outer tube 53 at an intermediate position of the shaft 51, and the core metal member 6 has a proximal-side end portion exposed to the outside through the opening portion 55 of the inner tube 54, bending of a distal portion of the shaft 51 inclusive of the balloon 52 can be effectively restrained, in the rapid exchange type balloon catheter 50.

In addition, where the support base 4 has the holding portion 31*b* that holds the shaft 51, and the core metal member 6 has a proximal-side end portion extending to the proximal side of the position at which the shaft 51 is held by the holding portion 31*b*, the core metal member 6 is held by the holding portion 31*b* of the support base 4 and, therefore, bending of the shaft 51 on the distal side of the holding portion 31*b* can be restrained more assuredly.

In addition, where the core metal member 6 has an outside diameter equal to, or smaller by 0.01 mm to 0.1 mm than, the inside diameter of the inner tube of the shaft 51, the core metal member 6 can be smoothly inserted into the inner tube 54, and the shaft 51 can be securely supported and restrained from bending.

In addition, where the core metal member 70 is formed in a curved shape in a state before insertion into the shaft 51, it is possible, with the core metal member 70 disposed in such a manner as to be projected toward the direction opposite to the bending direction of the shaft 51, to help ensure that bending of the shaft 51 and the curving of the core metal member 70 cancel each other, whereby the shaft 51 can be set more horizontal.

In addition, where the core metal member 70 has the flat surface portion 70*a* at a part of the circumferential surface thereof, the curving direction of the core metal member 70 can be reliably disposed to be oriented in the direction opposite to the bending direction of the shaft 51.

Note that the present invention is not limited to the aforementioned embodiment, and various modifications can be made by those skilled in the art within the technical thought of the present invention.

The detailed description above describes a balloon wrapping apparatus for wrapping a balloon of a balloon catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon wrapping method for wrapping a balloon of a balloon catheter provided with the balloon at a distal portion of an elongated shaft, the balloon wrapping method comprising:
    supporting a portion other than the distal portion of the elongated shaft with a holding portion on a grooved-shaped placing portion of a holding base section of a support base;
    inserting a core metal member into the elongated shaft, wherein the core metal member is inserted into the elongated shaft from a distal end position of the balloon to at least a proximal side of a proximal end position of the balloon;
    covering a part of the elongated shaft supported on the grooved-shaped placing portion of the holding base section with the holding portion;
    fixing a distal end of the core member to a holding member;
    inserting the balloon of the balloon catheter into a pleating section;
    fixing the holding member fixed to the distal end of the core member to an insertion portion of the pleating section;
    forming the balloon with wing shapes projecting in radial directions with the pleating section;
    inserting the balloon with the wing shapes projecting in radial directions into a folding section;
    fixing the holding member fixed to the distal end of the core member to a fixing insertion portion of the folding section; and
    folding the wing shapes formed in the balloon along a circumferential direction with the folding section after the forming the wing shapes projecting in the radial directions in the pleating section.

2. The balloon wrapping method according to claim 1, wherein the core metal member has an outside diameter equal to, or smaller by 0.01 mm to 0.1 mm than, an inside diameter of the inner tube of the elongated shaft.

3. The balloon wrapping method according to claim 1, further comprising:
    forming the core metal member in a curved shape in a state before insertion into the elongated shaft.

4. The balloon wrapping method according to claim 3, wherein the core metal member has a flat surface portion at a part of a circumferential surface of the core metal member.

5. The balloon wrapping method according to claim 1, wherein the core metal member has an elongated wire-like shape or a hollow shape.

6. The balloon wrapping method according to claim 1, wherein the core metal member is made of stainless steel, Ni—Ti alloys, or tungsten.

7. A balloon wrapping method for wrapping a balloon of a balloon catheter provided with the balloon at a distal portion of an elongated shaft, the balloon wrapping method comprising:
    supporting a portion other than the distal portion of the elongated shaft with a holding portion on a grooved-shaped placing portion of a holding base section of a support base;
    inserting a core metal member into the elongated shaft, wherein the core metal member is inserted into the elongated shaft from a distal end position of the balloon to at least a proximal side of a proximal end position of the balloon;
    covering a part of the elongated shaft supported on the grooved-shaped placing portion of the holding base section with the holding portion;
    fixing a distal end of the core member to a holding member;
    inserting the balloon of the balloon catheter into a pleating section;
    fixing the holding member fixed to the distal end of the core member to an insertion portion of the pleating section;
    forming the balloon with wing shapes projecting in radial directions with the pleating section;

inserting the balloon with the wing shapes projecting in radial directions into a folding section;

fixing the holding member fixed to the distal end of the core member to a fixing insertion portion of the folding section;

folding the wing shapes formed in the balloon along a circumferential direction with the folding section after the forming the wing shapes projecting in the radial directions in the pleating section; and providing the elongated shaft to have an inner tube and an outer tube disposed concentrically, with the inner tube extending to a proximal-side end portion of the elongated shaft, and wherein the core metal member has a length of at least twice a length of the balloon.

8. The balloon wrapping method according to claim 7, wherein the core metal member has an outside diameter equal to, or smaller by 0.01 mm to 0.1 mm than, an inside diameter of the inner tube of the elongated shaft.

9. The balloon wrapping method according to claim 7, further comprising:

forming the core metal member in a curved shape in a state before insertion into the elongated shaft.

10. The balloon wrapping apparatus according to claim 9, wherein the core metal member has a flat surface portion at a part of a circumferential surface of the core metal member.

11. The balloon wrapping method according to claim 7, wherein the core metal member has an elongated wire-like shape or a hollow shape.

12. The balloon wrapping method according to claim 7, wherein the core metal member is made of stainless steel, Ni—Ti alloys, or tungsten.

13. A balloon wrapping method for wrapping a balloon of a balloon catheter provided with the balloon at a distal portion of an elongated shaft, the balloon wrapping method comprising:

supporting a portion other than the distal portion of the elongated shaft with a holding portion on a grooved-shaped placing portion of a holding base section of a support base;

inserting a core metal member into the elongated shaft, wherein the core metal member is inserted into the elongated shaft from a distal end position of the balloon to at least a proximal side of a proximal end position of the balloon;

covering a part of the elongated shaft supported on the grooved-shaped placing portion of the holding base section with the holding portion;

fixing a distal end of the core member to a holding member;

inserting the balloon of the balloon catheter into a pleating section;

fixing the holding member fixed to the distal end of the core member to an insertion portion of the pleating section;

forming the balloon with wing shapes projecting in radial directions with the pleating section;

inserting the balloon with the wing shapes projecting in radial directions into a folding section;

fixing the holding member fixed to the distal end of the core member to a fixing insertion portion of the folding section;

folding the wing shapes formed in the balloon along a circumferential direction with the folding section after the forming the wing shapes projecting in the radial directions in the pleating section;

providing the elongated shaft to have an inner tube and an outer tube disposed concentrically, with the inner tube having an opening portion that opens to outside of the outer tube at an intermediate position of the elongated shaft; and exposing the proximal-side end portion of the core metal member to the outside of the elongated shaft through the opening portion of the inner tube.

14. The balloon wrapping method according to claim 13, wherein the core metal member has an outside diameter equal to, or smaller by 0.01 mm to 0.1 mm than, an inside diameter of the inner tube of the elongated shaft.

15. The balloon wrapping method according to claim 13, further comprising:

forming the core metal member in a curved shape in a state before insertion into the elongated shaft.

16. The balloon wrapping method according to claim 15, wherein the core metal member has a flat surface portion at a part of a circumferential surface of the core metal member.

17. The balloon wrapping method according to claim 13, wherein the core metal member has an elongated wire-like shape or a hollow shape.

18. The balloon wrapping method according to claim 13, wherein the core metal member is made of stainless steel, Ni—Ti alloys, or tungsten.

* * * * *